United States Patent
Fujie et al.

(10) Patent No.: US 10,474,188 B2
(45) Date of Patent: Nov. 12, 2019

(54) FLEXIBLE ELECTRONIC DEVICE CONTAINING ELECTRONIC ELEMENT AND POLYMER NANOSHEET AND METHOD FOR MANUFACTURING SAME

(71) Applicant: WASEDA UNIVERSITY, Shinjuku-ku, Tokyo (JP)

(72) Inventors: Toshinori Fujie, Tokyo (JP); Marin Okamoto, Tokyo (JP); Kento Yamagishi, Tokyo (JP); Atsushi Murata, Tokyo (JP); Shinji Takeoka, Tokyo (JP); Eiji Iwase, Tokyo (JP); Mizuho Kurotobi, Tokyo (JP); Hiroyasu Iwata, Tokyo (JP)

(73) Assignee: WASEDA UNIVERSITY, Tokyo (JP)

( * ) Notice: Subject to any disclaimer, the term of this patent is extended or adjusted under 35 U.S.C. 154(b) by 0 days.

(21) Appl. No.: 15/573,297

(22) PCT Filed: May 10, 2016

(86) PCT No.: PCT/JP2016/063841
§ 371 (c)(1),
(2) Date: Nov. 10, 2017

(87) PCT Pub. No.: WO2016/181958
PCT Pub. Date: Nov. 17, 2016

(65) Prior Publication Data
US 2018/0107244 A1    Apr. 19, 2018

(30) Foreign Application Priority Data
May 11, 2015  (JP) .................. 2015-096887

(51) Int. Cl.
*G06F 1/16* (2006.01)
*H01L 23/14* (2006.01)
(Continued)

(52) U.S. Cl.
CPC .......... *G06F 1/1613* (2013.01); *A61B 5/6801* (2013.01); *H01L 23/14* (2013.01);
(Continued)

(58) Field of Classification Search
CPC ..... G06F 1/1613; A61B 5/6801; H01L 23/14; H01L 23/145; H01L 23/31; H01L 23/3107
(Continued)

(56) References Cited

U.S. PATENT DOCUMENTS

2009/0250258 A1* 10/2009 Warigaya ............. H05K 3/3452
                                                                174/260
2012/0069584 A1   3/2012 Kawabe et al.
(Continued)

FOREIGN PATENT DOCUMENTS

JP   2010155919 A   7/2010
JP   2010161118 A   7/2010

OTHER PUBLICATIONS

Kenshi Numakura, 'Yoku Wakaru Flexible Electronics no Dekiru made', first edition, The Nikkan Kogyo Shinbun, Ltd., Dec. 22, 2010 (Dec. 22, 2010), pp. 33, 78, 120, 144.
(Continued)

*Primary Examiner* — Tremesha S Willis
(74) *Attorney, Agent, or Firm* — Fox Rothschild LLP

(57) ABSTRACT

Provided are an electronic device employing a polymer nanosheet, having an electronic element and a conductive wiring that are connected to each other in a solder-free manner, and exhibiting a high conformability and adhesiveness to an object for attaching including a biological tissue such as skin; and a method for manufacturing the same. The electronic device includes the electronic element; and the polymer nanosheet adhering to the electronic element. Specifically, the polymer nanosheet adheres to the electronic
(Continued)

element in a manner such that one surface of the electronic element is entirely covered by the polymer nanosheet. It is preferred that the polymer nanosheet have a thickness of smaller than 1 µm. Further, a conductive wiring capable of being electrically connected to the electronic element; and a power source for supplying power to the electronic element, may also be formed on the polymer nanosheet.

12 Claims, 14 Drawing Sheets

(51) Int. Cl.
| | |
|---|---|
| H01L 23/31 | (2006.01) |
| H01L 25/065 | (2006.01) |
| H05K 1/02 | (2006.01) |
| H05K 1/18 | (2006.01) |
| H05K 3/00 | (2006.01) |
| H01L 23/498 | (2006.01) |
| A61B 5/00 | (2006.01) |
| H05K 1/09 | (2006.01) |

(52) U.S. Cl.
CPC ............ *H01L 23/145* (2013.01); *H01L 23/31* (2013.01); *H01L 23/3107* (2013.01); *H01L 23/4985* (2013.01); *H01L 25/065* (2013.01); *H05K 1/0283* (2013.01); *H05K 1/189* (2013.01); *H05K 3/0014* (2013.01); *H05K 1/097* (2013.01); *H05K 2201/0145* (2013.01); *H05K 2201/0154* (2013.01); *H05K 2201/0158* (2013.01)

(58) Field of Classification Search
USPC ........................................................ 361/749
See application file for complete search history.

(56) References Cited

U.S. PATENT DOCUMENTS

| | | | |
|---|---|---|---|
| 2013/0118791 A1* | 5/2013 | Okamoto | ............... H05K 1/186 174/260 |
| 2013/0328100 A1 | 12/2013 | Kono et al. | |
| 2014/0374267 A1* | 12/2014 | Monteiro | ................. C25D 5/10 205/104 |

OTHER PUBLICATIONS

White paper on telecommunications 2014 by Ministry of Internal Affairs and Communications of Japan.
Bauer, S.: "Sophisticated skin", Nature Mater., 2013, 12, 971-872.
D. Kim, et al.: "Epidermal Electronics", Science, 2011, 333, 838-843.
M. Kaltenbrunner, et al.: "An ultra-lightweight design for imperceptible plastic electronics", Nature, 2013, 499, 458-463.
K. Fukuda, et al.: "Fully-printed high-performance organic thin-film transistors and circuitry on one-micron-thick polymer films", Nat. Commun., 2014, 5, 1-8.
International Search Report dated Jul. 26, 2016 in PCT/JP2016/063841.

* cited by examiner

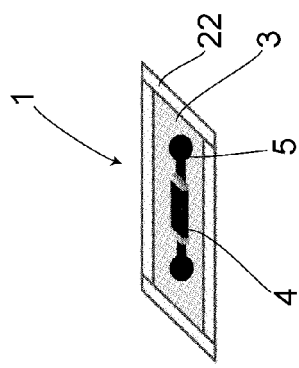
FIG.6D
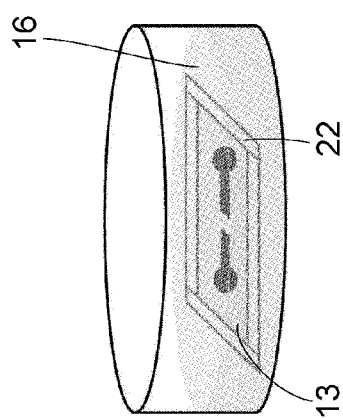
FIG.6C
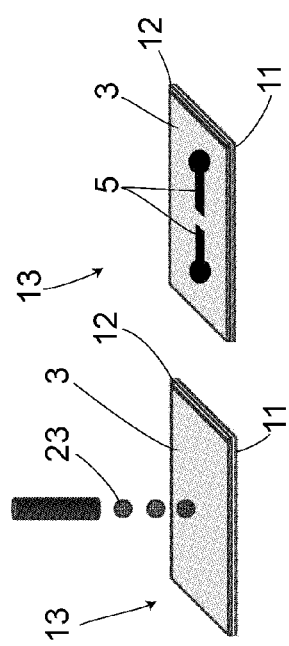
FIG.6B
FIG.6A

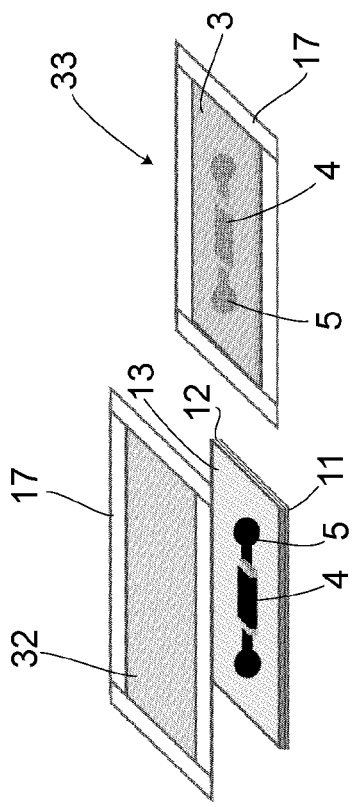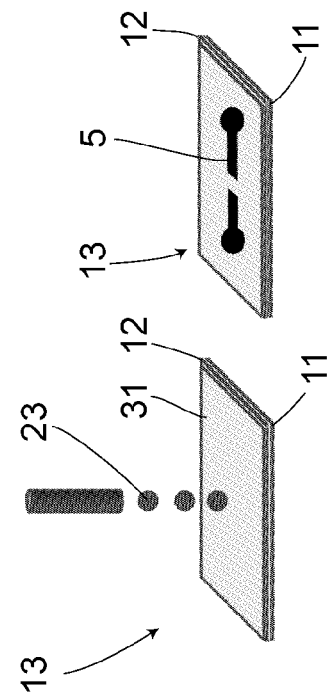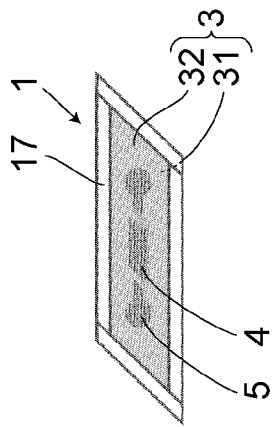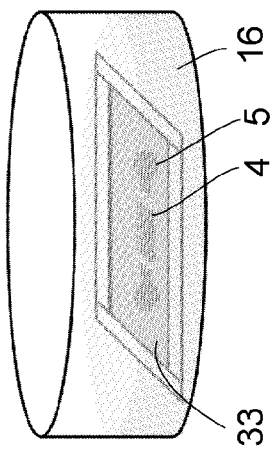

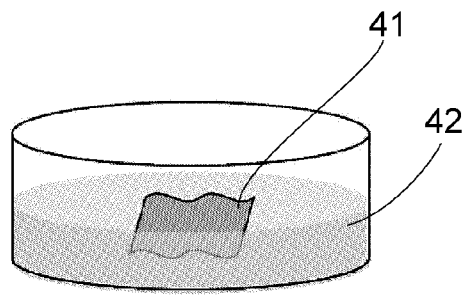 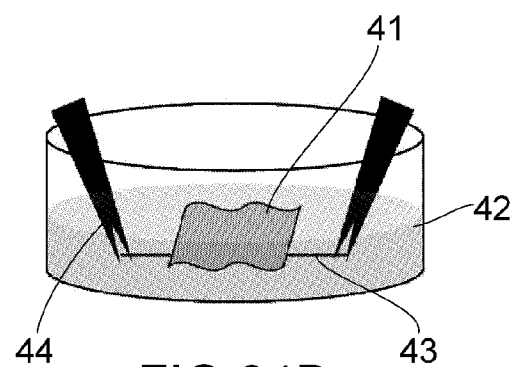
FIG.24A  FIG.24B
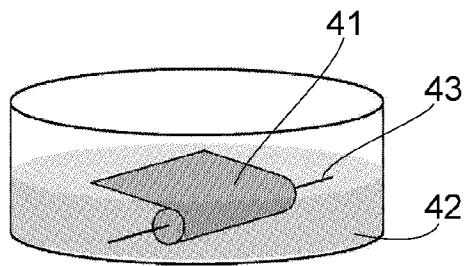 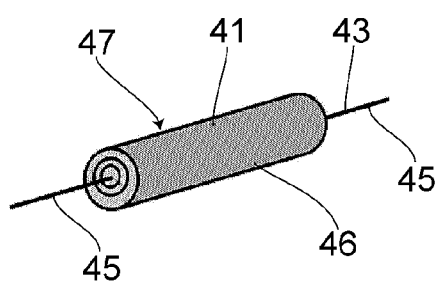
FIG.24C  FIG.24D
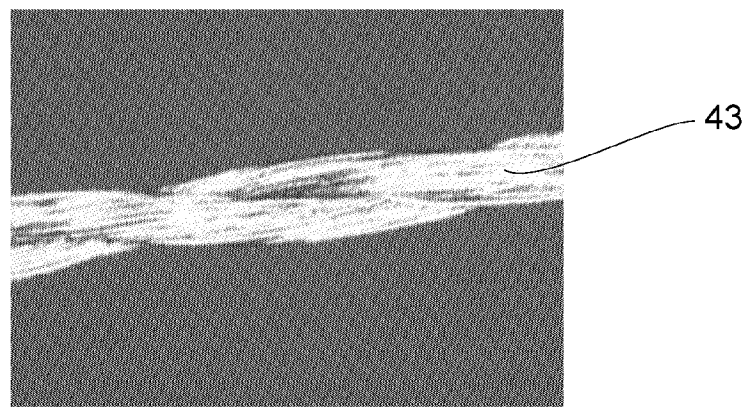
FIG.25

FLEXIBLE ELECTRONIC DEVICE CONTAINING ELECTRONIC ELEMENT AND POLYMER NANOSHEET AND METHOD FOR MANUFACTURING SAME

CROSS REFERENCE TO RELATED APPLICATIONS

This U.S. Application is a National Stage Entry of PCT/JP2016/063841 filed on May 10, 2016, which claims priority to Japanese Application No.: 2015-096887 filed May 11, 2015, the entirety of which is hereby incorporated herein by reference.

TECHNICAL FIELD

The present invention relates to an electronic device including an electronic element as a component; especially to a flexible electronic device capable of being attached to an object for attaching, and a method for manufacturing the same.

BACKGROUND ART

As for countries including our country that have entered or are entering super-aged society, it has been critically important to develop medical devices for maintaining and controlling healthy life expectancy. In recent years, wearable electronics for the purpose of continuously measuring biological information have been developed in an accelerated manner. And, wearable devices such as wristwatch-type heart rate meters and blood sugar level sensors have been put to practical use (e.g. Non-patent Literature 1).

There is also being developed a technique where a flexible substrate is used to directly fix an electronic device to an arm, a leg and other parts. For example, as an electronic device capable of undergoing curvature deformation, there has been proposed a flexible substrate that is formed using a resin film having a comb-like portion composed of a plurality of protrusions (e.g. Patent Literature 1). Further, there has also been proposed an LED device (e.g. Patent Literature 2) manufactured in the following manner. That is, a light-emitting diode is to be embedded in an encapsulation resin layer, followed by placing a barrier film layer thereon so as to form an encapsulation sheet, and then thermally compressing such encapsulation sheet onto a substrate through flat press.

As a more advanced configuration, studies have also been made on a type of device capable of acting like a sticker, and thus being attached to a highly stretchable biological tissue such as skin. It has been pointed out that by employing a thin film exhibiting the same level of stretching rate as epidermis, the device can be fixed to the skin without causing any uncomfortable feeling (e.g. Non-patent Literature 2).

Further, as examples of devices using thin films, there have been reported case examples where circuit boards were manufactured using thin films having a thickness of several μms, such as those made of polyvinyl alcohol, polyethylene naphthalate and parylene-C (e.g. Non-patent Literatures 3 to 5).

CITATION LIST

Non-Patent Literature

Non-patent Literature 1: White paper on telecommunications 2014 by Ministry of Internal Affairs and Communications of Japan Non-patent Literature 2: Bauer, S. Nature Mater., 2013, 12, 971-872.

Non-patent Literature 3: D. Kim, et al., Science, 2011, 333, 838-843.

Non-patent Literature 4: M. Kaltenbrunner, et al., Nature, 2013, 499, 458-463.

Non-patent Literature 5: K. Fukuda, et al., Nat. Commun., 2014, 5, 1-8.

Patent Literature

Patent Literature 1: JP-A-2012-69673
Patent Literature 2: JP-A-2013-258209

SUMMARY OF INVENTION

Technical Problem

However, with regard to each of the flexible devices described in Patent Literatures 1 and 2, a resin layer for encapsulating and holding an electronic element(s) is, for example, as thick as 300 μm or thicker. Therefore, none of the devices can be attached to a highly stretchable biological tissue such as skin.

Further, according to the descriptions in Non-patent Literatures 2 to 5, polyimide, polyvinyl alcohol, polyethylene naphthalate, parylene-C and the like are used as the materials for the flexible substrate thin film, and the thin film employed has a film thickness of about 1 to 30 μm. However, other than these descriptions, no mention is made on reducing the film thickness to less than 1 μm, nor the effects brought about thereby.

The present invention was made in view of these circumstances. It is an object of the invention to provide an electronic device having a smooth surface and a flexible structure, employing a thin film of a thickness of smaller than 1 μm and exhibiting a high conformability and a favorable adhesiveness to an object for attaching including a biological tissue such as skin; and a method for manufacturing such electronic device.

Further, it is also an object of the invention to provide an electronic device formed by allowing an electronic element(s) and a conductive wiring to physically adhere to a polymer nanosheet, and thereby electrically connecting these electronic element(s) and conductive wiring without performing any process such as soldering; and a method for manufacturing this electronic device.

Solution to Problem

In order to solve these problems, the electronic device of the present invention includes an electronic element; and a polymer nanosheet adhering to the electronic element.

Further, a method for manufacturing the electronic device of the invention includes: a step of forming a first polymer nanosheet on a substrate; a step of forming a conductive wiring on the first polymer nanosheet; a step of arranging an electronic element in a manner such that an electrode of the electronic element is capable of coming into contact with the conductive wiring; a step of bringing a second polymer nanosheet into a close contact with the first polymer nanosheet to stick the second polymer nanosheet to the first polymer nanosheet with the electronic element and the conductive wiring being sandwiched therebetween, and thus electrically connecting the electronic element and the conductive wiring; and a step of separating the substrate from the first polymer nanosheet.

Advantageous Effects of Invention

According to the electronic device provided by the present invention, the electronic element is stuck to the polymer nanosheet through an intermolecular force, thereby allowing the flexible electronic device to be attached to an object for attaching including a biological tissue such as skin in particular without using a glue or the like.

According to the method for manufacturing the electronic device of the present invention, there can be manufactured, through simple steps, a flexible electronic device that includes the electronic element as a component, and is capable of being attached to the object for attaching in particular.

BRIEF DESCRIPTION OF DRAWINGS

FIG. 5 is a series of diagrams showing a process for forming a polymer nanosheet base body of the first embodiment of the invention, wherein

FIG. 6 is a series of diagrams showing a process for completing the electronic device of the first embodiment of the invention, starting with the printing of the conductive wiring onto the polymer nanosheet, wherein FIG. 6A shows a step of ejecting a conductive material in an ink-jet manner; FIG. 6B shows a step of forming the polymer nanosheet base body on which the conductive wiring is formed; FIG. 6C shows a step of immersing the polymer nanosheet base body of FIG. 6B in water; and FIG. 6D shows a step of forming the electronic device by dissolving the sacrifice layer, and then separating the substrate from the polymer nanosheet.

FIG. 12 is a series of diagrams showing a process for manufacturing the electronic device of the second embodiment of the invention, wherein FIG. 12A shows a step of ejecting a conductive material in an ink-jet manner; FIG. 12B shows a step of forming a polymer nanosheet base body by forming the conductive wiring on a first polymer nanosheet; FIG. 12C shows a step of arranging the electronic element on the first polymer nano sheet on which the conductive wiring has been printed, and then covering such first polymer nanosheet with a second polymer nanosheet; FIG. 12D shows a step of forming a polymer nanosheet-stuck base body; FIG. 12E shows a step of immersing the polymer nanosheet-stuck base body in water; and FIG. 12F shows a step of forming the electronic device by dissolving a sacrifice layer, and then separating a substrate from the first polymer nanosheet.

FIG. 24 is a series of diagrams showing a process for manufacturing a jumper wiring of a third embodiment of the invention, wherein FIG. 24A shows a state where a nonconductive polymer nanosheet is immersed in water; FIG. 24B shows how a pair of tweezers is used to pinch both ends of a conductive thread so as to bring the same closer to the polymer nanosheet in water; FIG. 24C shows how the polymer nanosheet is to be wrapped around the conductive thread so as to cover the same; and FIG. 24D shows the jumper wiring with the conductive thread already being covered by the polymer nanosheet wrapped therearound.

FIG. 25 is a photograph showing the conductive thread made of a silver fiber in the third embodiment of the invention.

DESCRIPTION OF EMBODIMENTS

Figure 1:
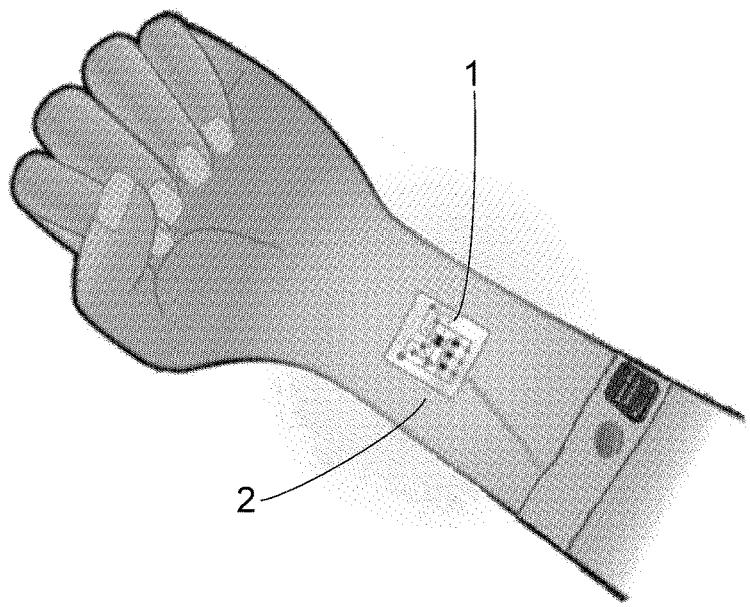
FIG. 1 is a schematic view showing a usage example where an electronic device using a polymer nanosheet has been attached to the inner side of an arm.

An electronic device and a method for manufacturing the same are described hereunder with reference to the accompanying drawings. FIG. 1 shows an example of use where an electronic device 1 using a later-described polymer nanosheet of the invention has been attached to the inner side of an arm as an object for attaching 2. When attached to the object for attaching 2 such as skin, this electronic device 1 can be used as an electronic device for biomedical purposes in a way such that the electronic device 1 is capable of measuring pulses and skin conductance, and sensing perspiration. By thinning down the polymer nanosheet of the invention to a thickness of smaller than 1 μm, the electronic device 1 can be made extremely thin, and attached without using a glue or the like so that there will not occur an unpleasant feeling by wearing the same. Here, the object for attaching 2 is not limited to human skin, but may also be, for example, an organ, a non-human animal or insect, food and an elastomer surface.

Figure 2:
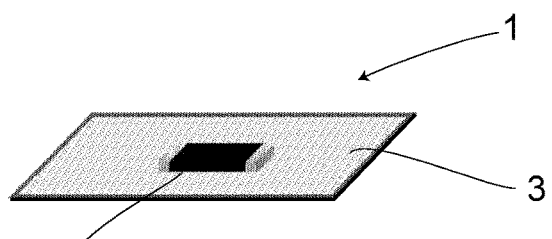
FIG. 2 is a perspective view showing an electronic device of a first embodiment of the invention, the electronic device now having an electronic element.

Next, a first embodiment of the invention is described with reference to FIG. 2 to FIG. 15. FIG. 2 is a perspective view showing an electronic device 1 of the first embodiment of the invention. The electronic device 1 includes an electronic element 4; and a polymer nanosheet 3 adhering to the electronic element 4. Particularly, the polymer nanosheet 3 adheres to the electronic element 4 in a manner such that one surface of the electronic element 4 is entirely covered by the polymer nanosheet 3. There may be employed one electronic element 4, or multiple electronic elements 4.

The electronic element(s) 4 adhere to the polymer nanosheet 3 through an intermolecular force. Further, since the polymer nanosheet 3 is now used, the electronic device 1 can be attached to the object for attaching 2 such as skin without the aid of a glue or the like. Furthermore, the polymer nanosheet 3 adheres to the electronic element 4 in the way such that one of the surfaces of the electronic element 4 is entirely covered by the polymer nanosheet 3. Therefore, the polymer nanosheet 3 is capable of conforming with the electronic element 4, thus improving an adhesiveness between the polymer nanosheet 3 and the electronic element 4.

Figure 3:
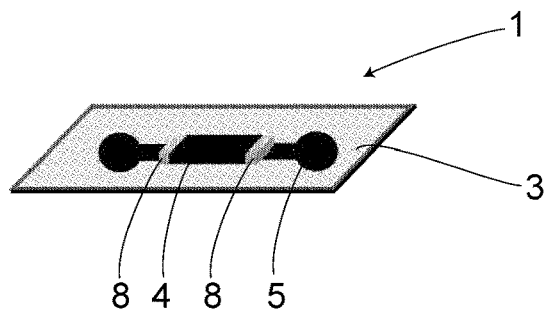
FIG. 3 is a perspective view showing the electronic device of the first embodiment of the invention, the electronic device now having the electronic element and a conductive wiring.

FIG. 3 shows another type of the electronic device 1. As compared to the electronic device 1 shown in FIG. 2, this electronic device 1 further includes a conductive wiring 5 that is formed on the polymer nanosheet 3 and is electrically connected to the electronic element 4. Since the polymer nanosheet 3 physically adheres to and is able to conform with the electronic element 4, the electronic element 4 is allowed to strongly adhere to the polymer nanosheet 3 through the intermolecular force. At that time, by arranging an electrode 8 of the electronic element 4 on the conductive wiring 5 formed on the polymer nanosheet 3, the conductive wiring 5 and the electrode 8 will be pressure-bonded to each other such that an intermolecular force between the conductive wiring 5 and the electrode 8 can also be strengthened. In this way, the conductive wiring 5 can be connected to the electrode 8 of the electronic element 4 through a strong adhesion force i.e. the conductive wiring 5 can be electrically connected to the electronic element 4 without performing any process such as soldering.

Examples of the electronic element 4 include active parts such as a light-emitting element (e.g. light-emitting diode (LED)), a transistor, a diode and an IC; and passive parts such as a resistor, an inductor and a condenser. Further, the electronic device 1 may also be manufactured by mounting various sensors such as a strain sensor and/or an RFID tag on the polymer nanosheet 3 in a manner such that they will adhere to the polymer nanosheet 3.

Figure 4:
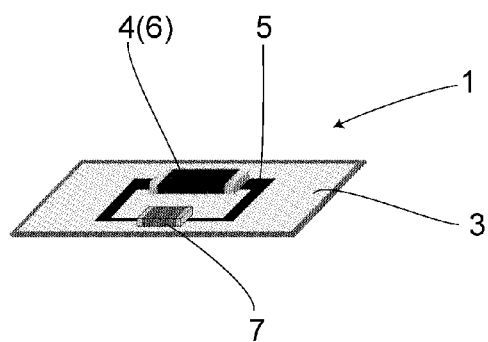
FIG. 4 is a perspective view showing the electronic device of the first embodiment of the invention, the electronic device now having the electronic element, the conductive wiring and a power source.

FIG. 4 shows another type of the electronic device 1. As compared to the electronic device 1 shown in FIG. 3, this electronic device 1 further includes a power source 7 that is arranged on the polymer nanosheet 3 and serves to supply electric power to an active part 6 as the electronic element 4. In this way, there can be provided an electronic device 1 integrally equipped with the power source 7 for supplying electric power to the active part 6. As such power source 7, there may be used batteries such as a solar battery; and a capacitor battery employing a large-capacity capacitor. Further, the power source 7 may also be that capable of supplying electric power to the electronic element 4 through an induction coil such as that used in a non-contact IC card.

As a material for the polymer nanosheet 3 used in the invention, there may be employed polymers such as a synthetic polymer, a natural polymer, a rubber and an elastomer. More specifically, it is preferred that the polymer nanosheet 3 be made of any one of polystyrene-isoprene-styrene, polydimethylsiloxane, silicone, polystyrene, polymethacrylate, polylactate, polylactic acid-glycolic acid copolymer, polyvinyl acetate, chitosan, alginic acid, cellulose acetate, hyaluronic acid, gelatin and collagen. By employing these kinds of materials, there can be provided an electronic device 1 exhibiting a high adhesiveness and stretchability with respect to the attachment target objet 2 such as skin. Here, as an example of a polymer nanosheet, the following document can be listed as a reference. T. Fujie and S. Takeoka, in Nanobiotechnology, eds. D. A. Phoenix and A. Waqar, One Central Press, United Kingdom, 2014, pp. 68-94.

Figure 5A:
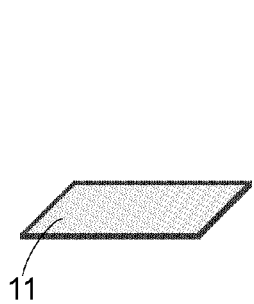
FIG. 5A shows a substrate on which the polymer nanosheet and others are to be formed.

Steps for manufacturing the electronic device of the present embodiment are described with reference to FIG. 5 and FIG. 6. As shown in FIG. 5A, prepared at first is a substrate 11 on which the polymer nanosheet 3 is to be formed. The substrate 11 will be separated from the polymer nanosheet 3 when attaching the electronic device 1 to the object for attaching 2 such as skin. As the substrate 11, there may be used, for example, PET (polyethylene phthalate), PP (polypropylene), PPE (polyphenylene ether), COP (cycloolefin), PI (polyimide), aluminum foil, conductive polymer membrane, paper, polysaccharide membrane, silicone resin, oblate (gelatin), silicon wafer and glass. In the present embodiment, a PET film (Lumirror 25T60 by PANAC Corporation) was used.

Figure 5B:
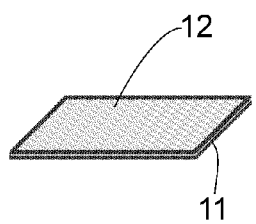
FIG. 5B shows a sacrifice layer formed to separate the substrate from the polymer nanosheet after the polymer nanosheet has been formed.

As shown in FIG. 5B, a sacrifice layer 12 is then formed on the substrate 11. This sacrifice layer 12 is used to separate the substrate 11 from the polymer nanosheet 3 after the polymer nanosheet 3 has been formed. A film forming method may employ either a roll-to-roll process using a gravure coater (not shown), or a process using a spin coater (not shown). The roll-to-roll process makes it possible to form a film at a larger area, as compared to the case where a spin coater is used. In the present embodiment, film forming was performed using a gravure coater (ML-120 by Yasui Seiki Inc.). The conditions for film forming were set to, for example, rotation frequency 30 rpm; linear speed 1.3 m/min; drying temperature 100° C. As a material for the sacrifice layer 12, a water-soluble polyvinyl alcohol (PVA by KANTO CHEMICAL CO., INC., 2 wt % in water) was used.

Figure 5C:
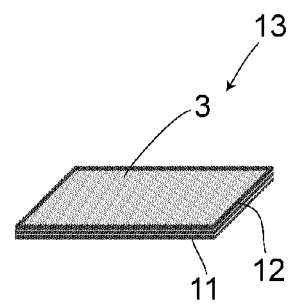
FIG. 5C shows the polymer nanosheet base body that has been formed by forming the polymer nanosheet on the sacrifice layer.

As shown in FIG. 5C, the polymer nanosheet 3 is to be formed on the sacrifice layer 12 so as to obtain a polymer nanosheet base body 13 composed of the substrate 11, the sacrifice layer 12 and the polymer nanosheet 3. It is preferred that the polymer nanosheet 3 have a thickness of smaller than 1 μm. When the thickness of the polymer nanosheet 3 is smaller than 1 μm, the polymer nanosheet 3 will exhibit a high conformability to the object for attaching 2 such as skin, thus improving the adhesiveness. Particularly, when the film thickness is not larger than 250 nm, a high conformability will be exhibited, and the adhesiveness will thus be improved as well. When the film thickness is not smaller than 1 μm, there will be exhibited a poor conformability to the electronic element 4 and the object for attaching 2. As is the case with the aforementioned sacrifice layer 12, the polymer nanosheet 3 may also be formed through a film forming method such as that involving the roll-to-roll process using a gravure coater (not shown), and that utilizing a spin coater. In the present embodiment, polystyrene butadiene styrene (SBS by Sigma Aldrich Japan, 3 wt % in tetrahydrofuran) was used. A film forming method employed was the roll-to-roll process using a gravure coater; and the conditions for film forming were set to rotation frequency 30 rpm; linear speed 1.3 m/min; drying temperature 100° C.

Next, as shown in FIG. 6A, a conductive material 23 will be ejected onto the polymer nanosheet 3; and as shown FIG. 6B, the conductive wiring 5 will then be formed on the polymer nanosheet 3. In the present embodiment, an ink-jet printer (DCP-J540N by Brother Industries, Ltd.) (not shown) was used to draw on the surface of the polymer nanosheet 3 a wiring pattern made of silver nanoparticles 21 (Drycure Ag-J by COLLOIDAL INK Co., Ltd., 4 mPa·s, particle size 15 nmφ)

Here, as a material for forming the conductive wiring 5, there can be used at least one material selected from, for example, metal nanoparticles, semiconductor nanoparticles, a conductive polymer and a nano-carbon material. Particularly, metal nanoparticles such as silver, gold, copper and nickel nanoparticles are preferred, because they are relatively easily available and are materials with low resistivities. Further, with regard to a method for forming the wiring pattern, instead of ink-jet printing, simple methods such as offset printing and screen printing may be employed to print and form the conductive wiring 5 on the polymer nanosheet 3.

Next, as shown in FIG. 6C, a frame 22 made of a paper tape will be provided on the circumference of the polymer nanosheet base body 13 of FIG. 6B on which the conductive wiring 5 has been printed, followed by immersing such polymer nanosheet base body 13 in a stripping liquid 16 made of water, for example. This step causes the sacrifice layer 12 to dissolve, and thus allows the substrate 11 to be separated from the polymer nanosheet 3.

Next, as shown in FIG. 6D, the electronic device 1 can then be manufactured by allowing the electronic element 4 to adhere to the polymer nanosheet 3, and be electrically connected to the conductive wiring 5.

Figure 7:
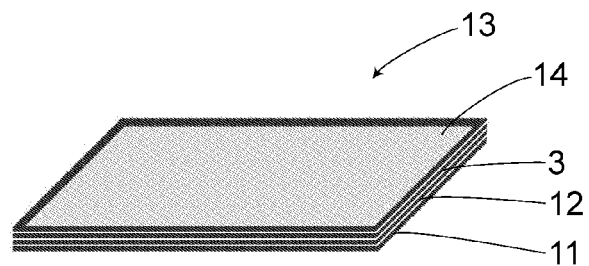
FIG. 7 is a diagram showing an ink absorbing layer that has been formed on the polymer nanosheet before printing the conductive wiring in the first embodiment of the invention.

Here, as shown in FIG. 7, an ink absorbing layer 14 may be further formed on the polymer nanosheet base body 13 before printing the conductive wiring 5. It is desired that this ink absorbing layer be made of chitosan, polyvinyl acetate, cellulose acetate, gelatin, silica or cationic acrylic copolymer. By printing the conductive wiring 5 on the ink absorbing layer 14, the fine conductive wiring 5 can be formed more precisely, without having an ink containing the conductive material 23 repelled. In the present embodiment, a cationic acrylic copolymer (NS-600X by Takamatsu Oil & Fat Co., Ltd.) was used as the ink absorbing layer 14. As are the cases with the abovementioned sacrifice layer 12 and the polymer nanosheet 3, a film forming method employed was the roll-to-roll process using a gravure coater; and the conditions for film forming were set to rotation frequency 30 rpm; linear speed 1.3 m/min; drying temperature 100° C.

However, the sacrifice layer 12 does not necessarily have to be formed. For example, there may be employed a substrate 11 and a polymer nanosheet 3 that are relatively poorly adhesive to each other. In such case, by, for example, using a paper tape-made frame formed around the polymer nanosheet base body 13, the polymer nanosheet 3 can likewise be separated from the substrate 11 without the sacrifice layer 12.

Figure 8:
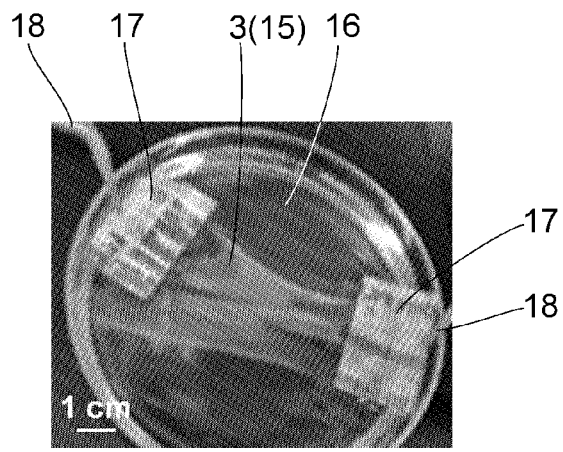
FIG. 8 is a photograph showing a state where the polymer nanosheet has been stretched by a pair of tweezers with paper being attached to both ends of the polymer nanosheet in the first embodiment of the invention.

FIG. 8 is a photograph of a SBS nanosheet 15 as the polymer nanosheet 3 having a self-supportability. The SBS nanosheet 15 was formed by at first immersing the polymer nanosheet base body 13 in water 16 so as to dissolve the PVA layer as the sacrifice layer 12, and then removing the PET film as the substrate 11. FIG. 8 shows a state where a paper 17 has been attached to both ends of the SBS nanosheet 15, and the SBS nanosheet 15 itself has been stretched by a pair of tweezers. Various SBS nanosheets 15 were prepared by changing the concentration of a SBS solution, and each SBS nanosheet 15 stripped was then attached to a smooth silicon substrate so as to measure the film thickness thereof through an atomic force microscope (AFM). As a result, it was confirmed that the film thickness of the SBS nanosheet 15 increased depending on the concentration of SBS. The SBS nanosheet 15 prepared exhibited a high stretchability, and an elastic modulus (40 MPa, film thickness 212 nm) about 20 times lower than that of a nanosheet made of polystyrene as a composition unit of SBS.

Figure 9:
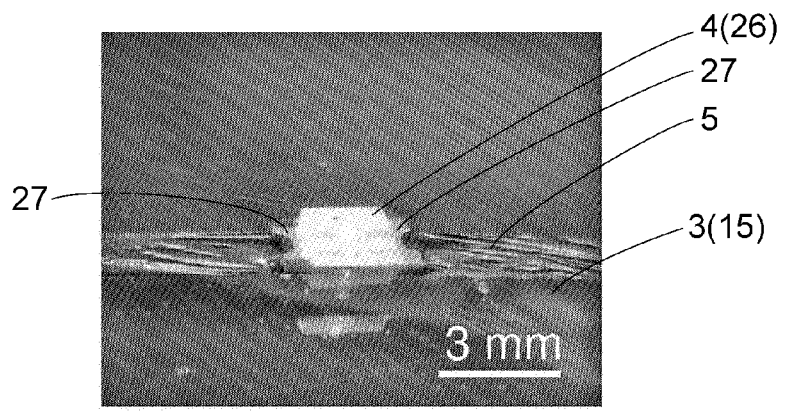
FIG. 9 is a photograph showing a state where an LED has been lighted in the first embodiment of the invention, the LED being already connected to the conductive wiring on the polymer nanosheet.
Figure 10:
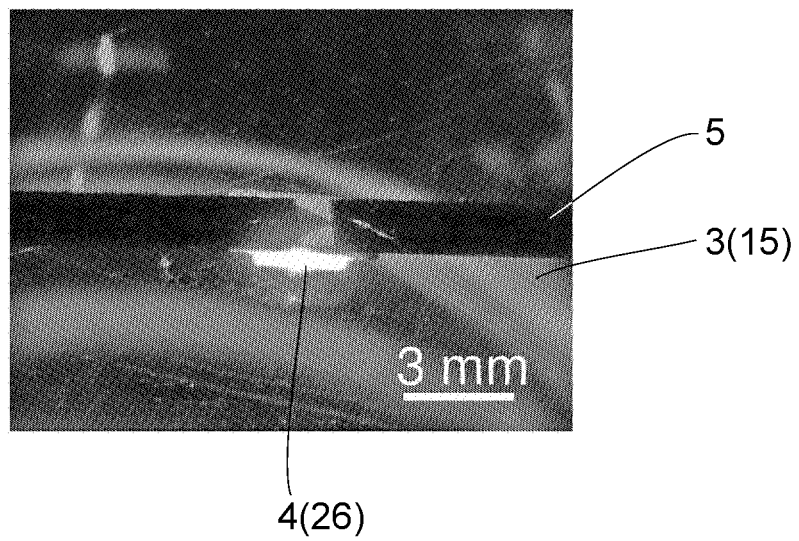
FIG. 10 is a photograph showing how the LED and the conductive wiring are connected to each other in the first embodiment of the invention, the photograph having been taken from a side opposite to the side where the LED is arranged.

FIG. 9 and FIG. 10 are photographs showing how a surface-mounted LED 26 (1.5 mm×3.0 mm×0.6 mm) emits light. The LED 26 serves as the electronic element 4, and is arranged on and physically and electrically fixed to the polymer nanosheet 3 on which the conductive wiring 5 has been printed. FIG. 9 is a photograph taken from a side where the LED 26 is provided, whereas FIG. 10 is a photograph taken from a rear surface side thereof. These photographs indicate that the conductive wiring 5 was able to flexibly conform with the electrode portion 27 of the LED 26.

Normally, the polymer nanosheet 3 is to be attached to the object for attaching 2 in a way such that the surface of the polymer nanosheet 3 that carries the electronic element 4 will become the top surface. However, the side carrying the electronic element 4 may also be attached to the object for attaching 2 instead. Under such configuration, a top surface will be the surface of the polymer nanosheet 3 under which the electronic element 4 is covered, thereby making it possible to protect the electronic element 4 from the outside.

Figure 11:
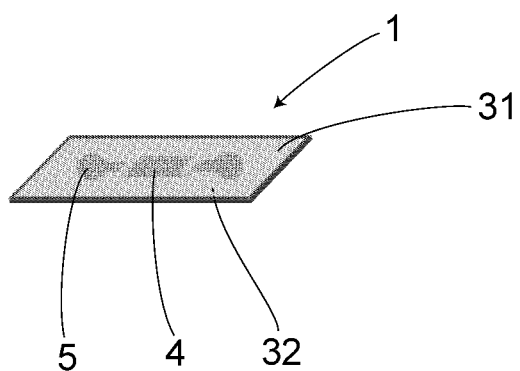
FIG. 11 is a perspective view showing an electronic device of a second embodiment of the invention, the electronic device now having an electronic element and a conductive wiring.

Next, a second embodiment of the invention is described with reference to FIG. 11 to FIG. 23. Here, elements identical to those in the first embodiment are given identical reference numerals, and the detailed descriptions thereof are thus omitted. FIG. 11 is a schematic view showing an electronic device 1 of the present embodiment; FIG. 12 is a series of schematic views showing an example of process for manufacturing the electronic device 1; FIG. 13 to FIG. 17 are diagrams showing evaluation results of the properties of the polymer nanosheet 3 obtained in the present embodiment, the polymer nanosheet 3 having the conductive wiring 5 made of the silver nanoparticles 21; and FIG. 18 to FIG. 23 are photographs showing the actual electronic device 1 manufactured.

The present embodiment and the first embodiment share an identical basic structure where the electronic element 4, the conductive wiring 5 and the power source 7 are arranged on the polymer nanosheet 3. However, the present embodiment differs from the first embodiment in that the electronic element 4 and others are now to be arranged on a first polymer nanosheet 31, and such first polymer nanosheet 31 is then brought into a close contact with and stuck to a second polymer nanosheet 32 i.e. the electronic element 4 and others are now sandwiched between the first polymer nanosheet 31 and the second polymer nanosheet 32.

As shown in FIG. 11 and FIG. 12, the electronic element 4 and the conductive wiring 5 are arranged on the first polymer nanosheet 31. However, as is the case with the first embodiment, there may be arranged on the first polymer nanosheet 31 only the electronic element 4; or the electronic element 4, the conductive wiring 5 and the power source 7. By sandwiching the electronic element 4 between the two first polymer nanosheet 31 and second polymer nanosheet 32, not only the adhesiveness between the polymer nanosheet (first polymer nanosheet 31 and second polymer nanosheet 32) and the electronic element 4 can be improved, but the electronic element 4 itself can be physically protected from the outside.

Here, it is also preferred that each of the first polymer nanosheet 31 and the second polymer nanosheet 32 have a thickness of smaller than 1 µm.

Further, it is preferred that each of the first polymer nanosheet 31 and the second polymer nanosheet 32 be made of any one of polystyrene-isoprene-styrene, polydimethylsiloxane, silicone, polystyrene, polymethacrylate, polylactate, polylactic acid-glycolic acid copolymer, polyvinyl acetate, chitosan, alginic acid, cellulose acetate, hyaluronic acid, gelatin and collagen.

Next, steps for manufacturing the electronic device 1 of the present embodiment are described with reference to FIG. 12. In the manufacturing steps shown below, steps shown in FIG. 12A and FIG. 12B are similar to the steps shown in FIG. 6A and FIG. 6B of the first embodiment. Specifically, FIG. 12A shows how the conductive material 23 is ejected through inkjet method; and FIG. 12B shows a state where the conductive wiring 5 has already been formed on the first polymer nanosheet 31 of the polymer nanosheet base body 13.

As shown in FIG. 12C, the electronic element 4 will then be arranged on the first polymer nanosheet 31 on which the conductive wiring 5 has been printed, followed by allowing such electronic element 4 to adhere to the first polymer nanosheet 31, and electrically connecting such electronic element 4 to the conductive wiring 5. Next, there is prepared the second polymer nanosheet 32 to be stuck to the first polymer nanosheet 31. At that time, a frame 17 made of a paper tape is provided around the second polymer nanosheet 32. In this way, as shown in FIG. 12D, the first polymer nanosheet 31 and the second polymer nanosheet 32 will then be stuck together so as to obtain a polymer nanosheet-stuck base body 33.

Steps shown in FIG. 12E and FIG. 12F are similar to the steps shown in FIG. 6C and FIG. 6D of the first embodiment. As shown in FIG. 12E, the polymer nanosheet-stuck base body 33 shown in FIG. 12D will be immersed in the stripping liquid 16 made of water, for example. This step causes the sacrifice layer 12 to dissolve, and allows the substrate 11 to then be separated from the first polymer nanosheet 31, thereby obtaining an electronic device 1 shown in FIG. 12F.

Here, as is the case with the first embodiment, the step for forming the sacrifice layer 12 can be omitted. For example, there may be employed a substrate 11 and a first polymer nanosheet 31 that are relatively poorly adhesive to each other. In such case, by, for example, using a paper tape-made frame formed around the second polymer nanosheet 32, the first polymer nanosheet 31 can likewise be separated from the substrate 11 without the sacrifice layer 12.

As described above, the electronic device 1 of the present embodiment is configured in a way such that the electronic element 4 is sandwiched between the first polymer nanosheet 31 and the second polymer nanosheet 32. According to the abovementioned method for manufacturing the electronic device 1, the electronic device 1 employing the polymer nanosheet 3 can be manufactured through simple steps.

Further, as described in the first embodiment, the ink absorbing layer 14 may further be provided on at least one of the first polymer nanosheet 31 and the second polymer nanosheet 32, and the conductive wiring 5 may then be printed on such ink absorbing layer 14.

Figure 13:
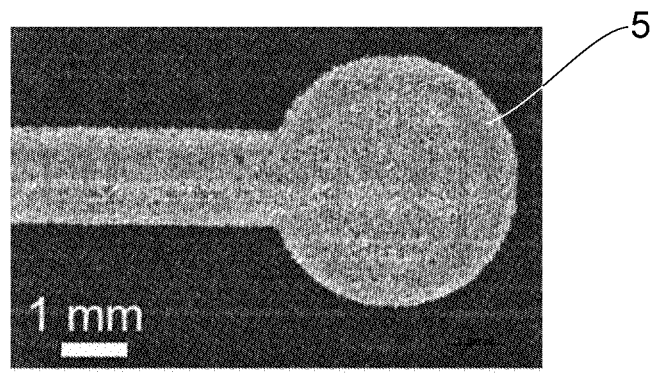
FIG. 13 is a diagram showing the conductive wiring made of silver nanoparticles in the second embodiment of the invention.
Figure 14:
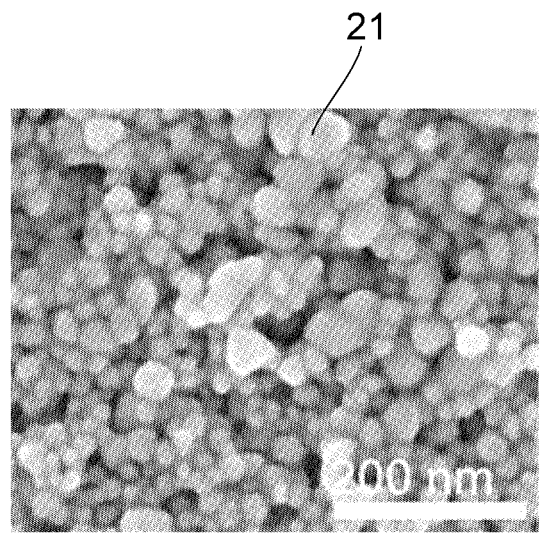
FIG. 14 is a SEM photograph of the conductive wiring made of the silver nanoparticles in the second embodiment of the invention.

Described hereunder is an example of the property evaluation of the polymer nanosheet 3 that is obtained in the present embodiment and has the conductive wiring 5 made of the silver nanoparticles 21. At first, a cationic ink absorbing layer 14 (film thickness: 115±26 nm) was formed on the surface of the SBS nanosheet 15 (film thickness: 383±21 nm) as the first polymer nanosheet 31 that had been formed on the PET film serving as the substrate 11. Next, as shown in FIG. 13, ink-jet printing was utilized to form the conductive wiring 5 (thickness 159±55 nm, line width: >0.37 mm) made of the silver nanoparticles 21. As shown in FIG. 14, as a result of observing such conductive wiring 5 through a scanning electron microscope (SEM), it was confirmed that the conductive wiring 5 was an integrated body of the silver nanoparticles 21.

Figure 15:
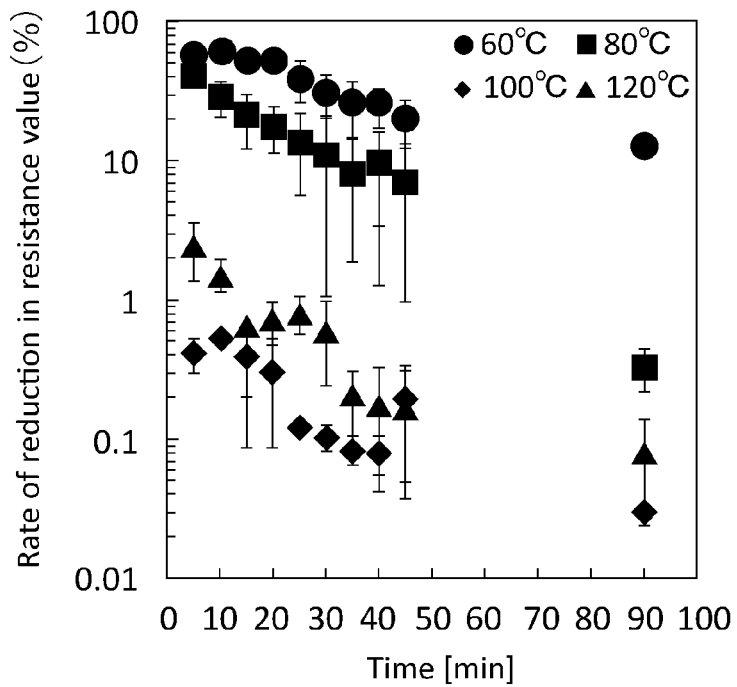
FIG. 15 is a graph showing a correlation between time and a rate of reduction in resistance value after the conductive wiring has gone through a heat treatment at given temperatures in the second embodiment of the invention.
Figure 16:
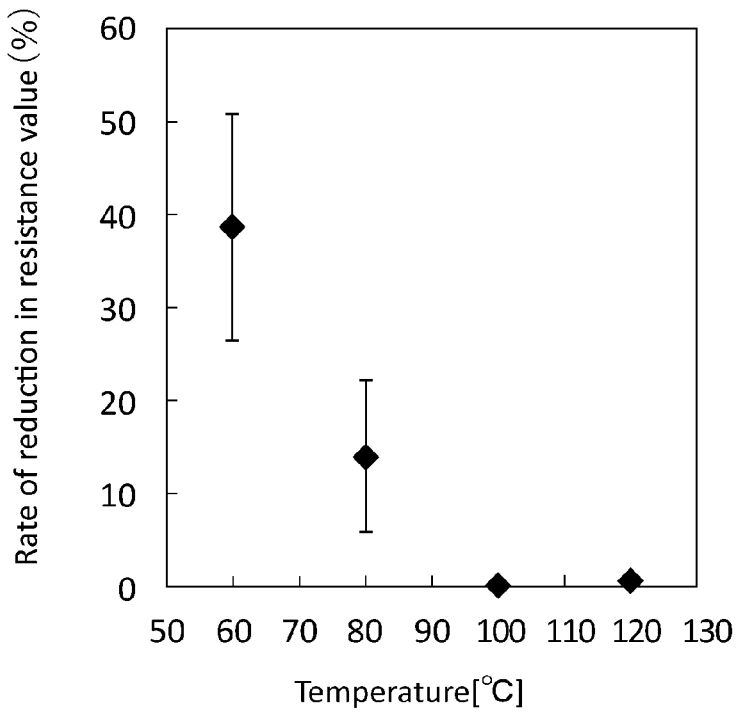
FIG. 16 is a graph showing a correlation between temperature and a rate of reduction in resistance value after the conductive wiring has gone through a heat treatment at given temperatures for 25 min each, in the second embodiment of the invention.

Further, as shown in FIG. 15, after performing a heat treatment on the SBS nanosheet 15 on which the conductive wiring 5 had been formed, a resistance value of the conductive wiring 5 dropped by at least three digits. Particularly, the resistance value decreased more significantly in heat treatments performed at temperatures of not lower than 100° C. than in heat treatments performed at temperatures of not higher than 80° C. As shown in FIG. 16, it became clear that the sheet resistance had decreased from $1.22 \times 10^4$ Ω/sq to 10.5 Ω/sq after performing the heat treatment for 25 min or longer, the value $1.22 \times 10^4$ Ω/sq being a sheet resistance value prior to the heat treatment.

Figure 17:
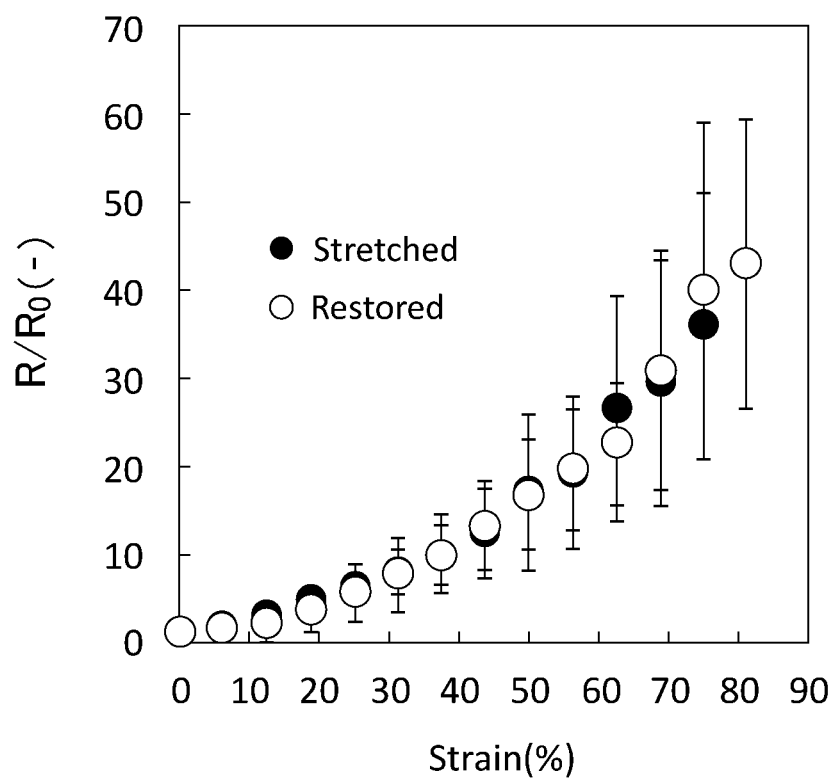
FIG. 17 is a graph showing a correlation between strain and a change in resistance value when the conductive wiring has been stretched and then restored in the second embodiment of the invention.

Also, the stretchability of the SBS nanosheet 15 was utilized in a way such that the SBS nanosheet 15 was stretched and then restored so as to measure a change in the resistance value of the conductive wiring 5. As shown in FIG. 17, a reversible change in the resistance value was exhibited even after the SBS nanosheet 15 had been stretched by 180% or greater. Thus, it was confirmed that the SBS nanosheet 15 having the conductive wiring 5 was superior in conductivity and stretchability. Due to these properties, it is anticipated that the SBS nanosheet 15 having the conductive wiring 5 will be able to be used as the electronic device 1 such as a circuit board and a strain gauge.

Here, the aforementioned resistance value measurement was performed in accordance with the present embodiment. That is, there was used a specimen where the conductive wiring 5 was sandwiched between the first polymer nanosheet 31 and the second polymer nanosheet 32 (an SBS nanosheet similar to the first polymer nanosheet 31). However, if the electronic device 1 is used as, for example, a circuit board or a strain gauge, the specimen may also be a single-layered nanosheet as is the case in the first embodiment.

Figure 18:
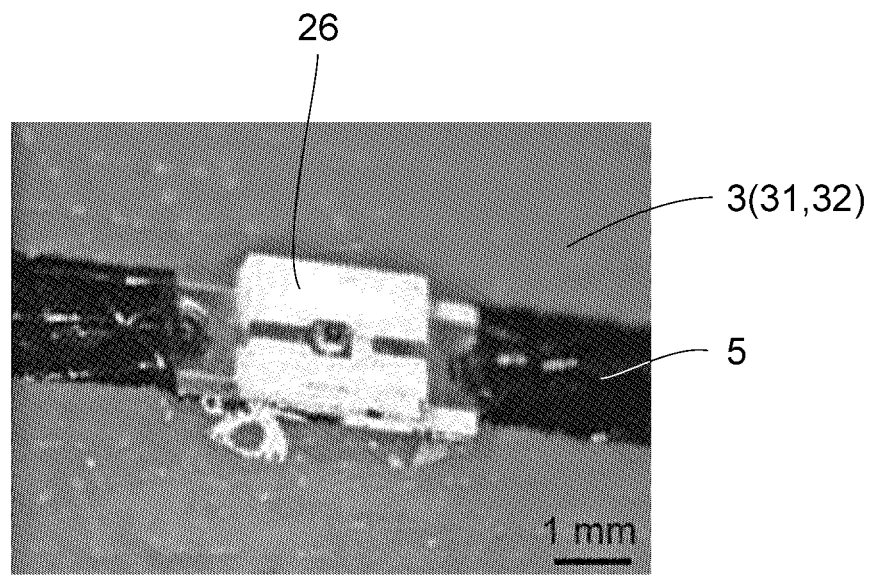
FIG. 18 is a photograph showing a state in the second embodiment of the invention, where an LED has now been physically and electrically fixed after arranging such LED on the first polymer nanosheet on which the conducive wiring had been printed, and then covering the surface of such first polymer nanosheet with a second polymer nanosheet.
Figure 19:
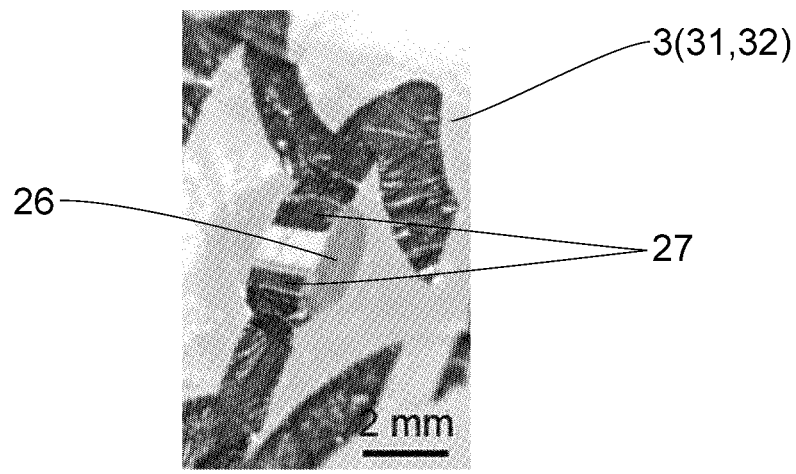
FIG. 19 is a photograph showing how the conductive wiring is capable of flexibly conforming with an electrode portion of the LED in the second embodiment of the invention, the photograph having been taken from a backside.
Figure 20:
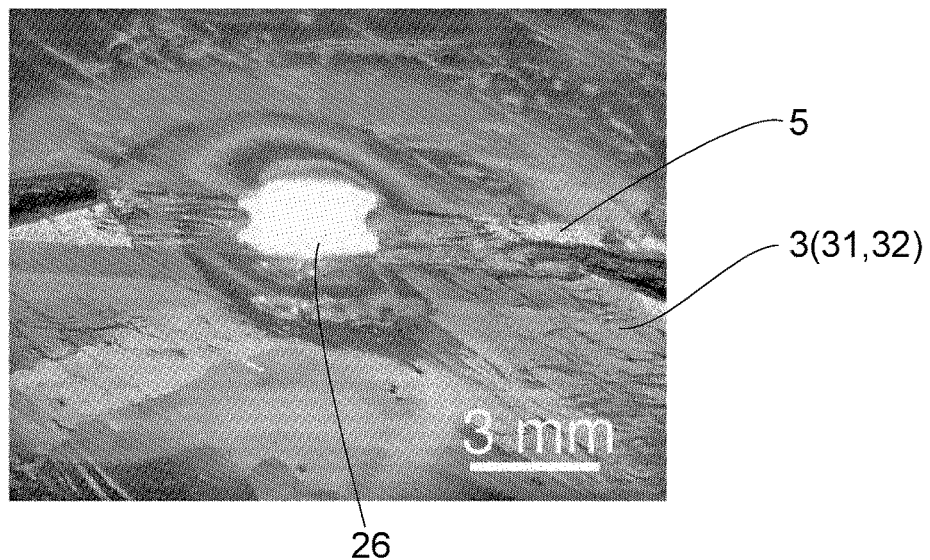
FIG. 20 is a photograph showing how the LED emits light in the second embodiment of the invention.
Figure 21:
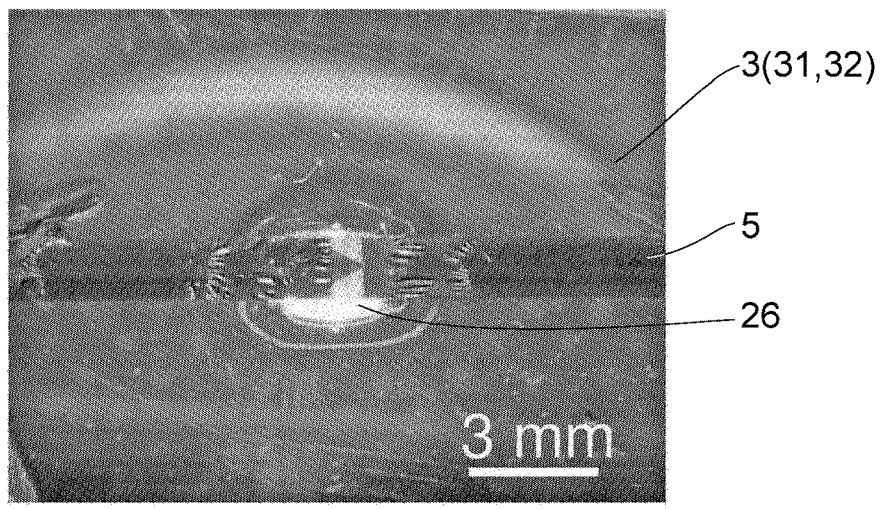
FIG. 21 is a photograph showing how the lighted LED and the conductive wiring are connected to each other in the second embodiment of the invention, the photograph having been taken from the backside.

As shown in FIG. 18, a surface-mounted LED 26 similar to that of the first embodiment was now arranged on an SBS-made first polymer nanosheet 31 on which the conductive wiring 5 had been printed. Further, the surface of such LED 26 was covered by another SBS-made second polymer nanosheet 32 such that the LED 26 was able to be physically and electrically fixed. The conductive wiring 5 and the LED 26 were then observed from the rear side of an SBS-made polymer nanosheet 3 comprising these nanosheets that had adhered to each other. As shown in FIG. 19, it was confirmed that the conductive wiring 5 had been able to flexibly conform with the electrode portion 27 of the LED 26. As shown in FIG. 20 and FIG. 21, the LED 26 sandwiched between the first polymer nanosheet 31 and the second polymer nanosheet 32 was able to emit light without the aid of a chemical bonding such as that established by performing soldering.

Figure 22:
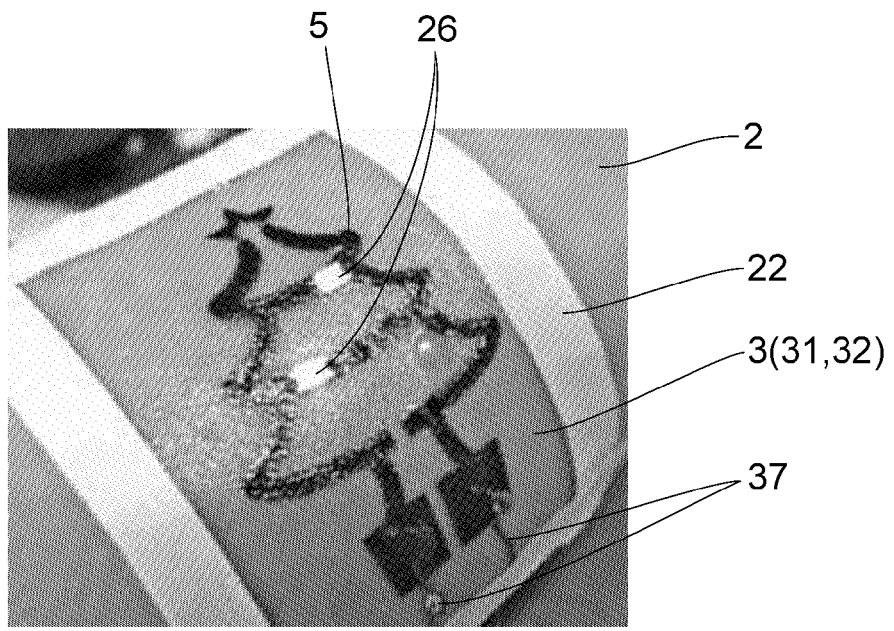
FIG. 22 is a photograph showing a state in the second embodiment of the invention, where the electronic device formed of the polymer nano sheet equipped with the LED is attached to the skin surface.
Figure 23:
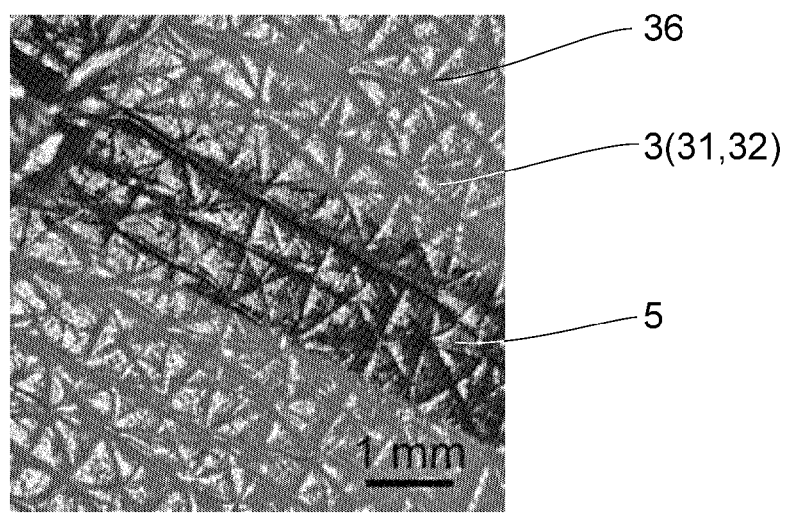
FIG. 23 is a photograph showing how the conductive wiring is even able to conform with the inner sides of the skin grooves in the second embodiment of the invention.

Further, the action of the LED 26 and the adhesiveness of the electronic device 1 to the skin surface as the object for attaching 2 were tested. There, the electronic device 1 used was that made of the polymer nanosheet 3 equipped with the LED 26. As shown in FIG. 22, due to the paper tape-made frame 22 provided around the polymer nanosheet 3, the electronic device 1 was able to be attached to the skin surface without causing cracks. Moreover, as a result of drawing a conductive wire 37 out of the electronic device 1 and then connecting the same to a 3V battery, lighting of the LED 26 at two locations on the skin surface was confirmed. In addition, as shown in FIG. 23, the conductive wiring 5 was even able to conform with the inner sides of skin grooves 36, which indicated a high conformability of the SBS-made polymer nanosheet 3.

Figure 26:
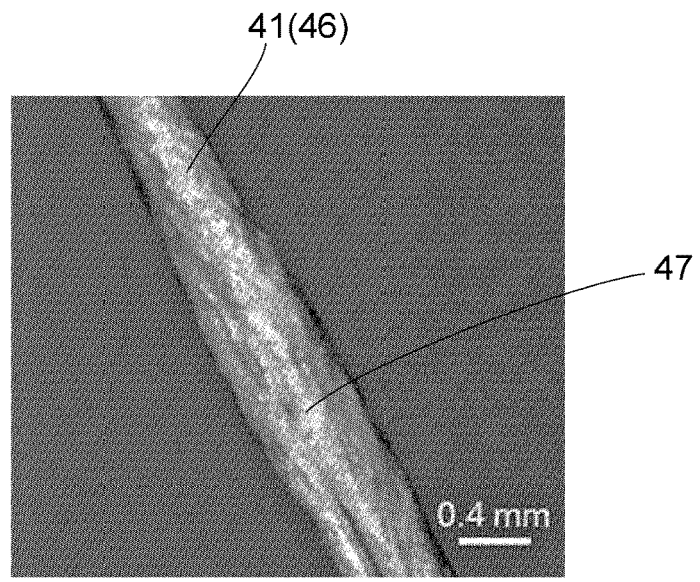
FIG. 26 is a photograph showing the jumper wiring obtained by covering the conductive thread with the polymer nanosheet made of polylactate in the third embodiment of the invention.
Figure 27:
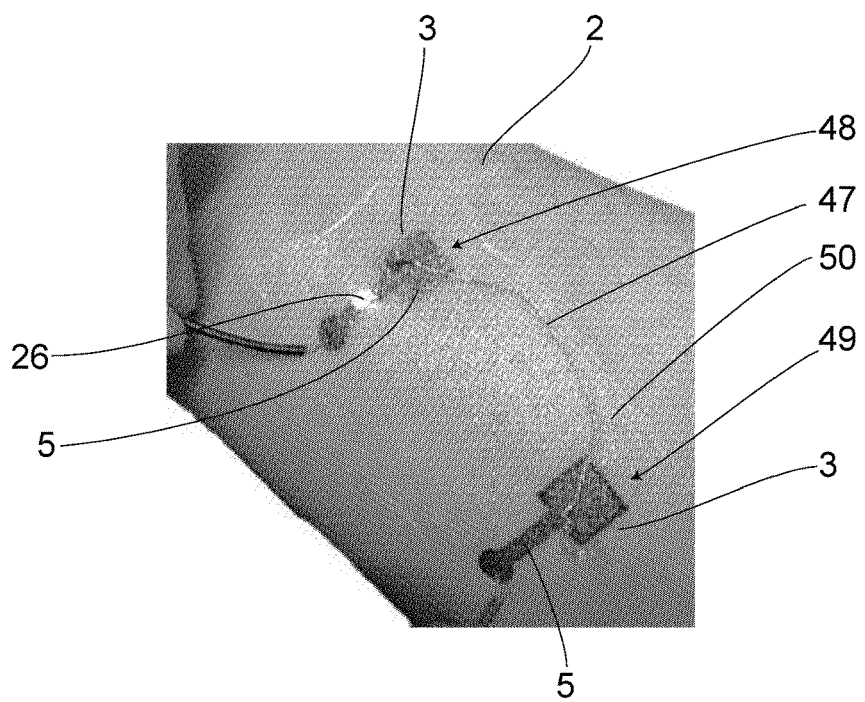
FIG. 27 is a photograph showing a composite electronic device obtained by electrically connecting multiple electronic devices through the jumper wiring in the third embodiment of the invention.

Next, a third embodiment of the invention is described with reference to FIG. 24 to FIG. 27. Here, elements identical to those in the first or second embodiment are given identical reference numerals, and the detailed descriptions thereof are thus omitted. FIG. 24 is a series of schematic views showing a process for manufacturing a jumper wiring 47 employing a polymer nanosheet 41; FIG. 25 to FIG. 27 are photographs showing the actual jumper wiring 47 and a composite electronic device 50 manufactured.

At first, as shown in FIG. 24A, the nonconductive polymer nanosheet 41 is to be immersed in a water 42. Next, as shown in FIG. 24B, a pair(s) of tweezers 44 were used to hold both ends of a conductive thread 43 so as to bring the same close the polymer nanosheet 41 in the water 42. In this way, as shown in FIG. 24C, the polymer nanosheet can then be wrapped around the conductive thread 43 so as to cover the same. Thus, as shown in FIG. 24D, there can be obtained the jumper wiring 47 having a conductive region 45 composed of the two ends of the conductive thread 43; and a nonconductive region 46 where the conductive thread 43 is covered by the polymer nanosheet 41.

In the present embodiment, a conductive thread made of a silver fiber (AGPOSS thread by Mitsufuji Corporation) was used as the conductive thread 43. FIG. 25 shows the conductive thread 43 that has not yet been covered by the polymer nanosheet; FIG. 26 shows the nonconductive region 46 where the conductive thread 43 is now covered by the polymer nanosheet 3 made of polylactate.

This jumper wiring 47 can, for example, be bonded to the conductive wiring 5-equipped polymer nanosheet 3 of any of the first and second embodiments. As shown in FIG. 27, the jumper wiring 47 was used to electrically connect: a first electronic device 48 having the LED 26 mounted on the polymer nanosheet 3; and a second electronic device 49 having the conductive wiring 5 formed on the polymer nanosheet 3. Here, by applying a voltage thereto, the lighting of the LED 26 was confirmed i.e. electrical conduction was able to be verified. In this way, the composite electronic device 50 can be obtained by electrically connecting the multiple electronic devices 48 and 49 that are physically and electrically arranged apart from each other, through the jumper wiring 47 partially covered by the polymer nanosheet 41.

According to the aforementioned electronic device 1 of the first embodiment and the method for manufacturing the same, this electronic device 1 with a high conformability is capable of being attached to the object for attaching 2 such as skin without a glue or the like. At the time of attaching the electronic device 1 to the object for attaching 2, the electronic element 4 has already been bonded to the polymer nanosheet 3 having a film thickness of smaller than 1 μm through the intermolecular force.

Further, the conductive wiring 5 and the power source 7 are to be formed on the polymer nanosheet 3, thereby making it possible to obtain the electronic device 1 carrying the active part 6 without performing soldering or the like.

Furthermore, by printing the conductive wiring 5 on the ink absorbing layer 14, the ink containing the conductive material 23 will no longer be repelled, thus allowing the fine conductive wiring 5 to be formed more precisely.

Furthermore, according to the electronic device 1 of the second embodiment and the method for manufacturing the same, by sandwiching the electronic element 4 and others between the first polymer nano sheet 31 and the second polymer nanosheet 32, not only the adhesiveness between the polymer nanosheet 3 and the electronic element 4 can be improved, but the electronic element 4 can be physically protected from the outside as well.

Furthermore, according to the jumper wiring 47 of the third embodiment, the nonconductive polymer nanosheet 41 is used to partially cover the conductive thread 43 so as to form the jumper wiring 47 having the conductive region 45 and the nonconductive region 46. The jumper wiring 47 serves to electrically connect the multiple electronic devices 48 and 49 that are physically and electrically arranged apart from each other. In this way, there is obtained the composite electronic device 50 including the multiple electronic devices 48 and 49.

The present invention has been so far described with reference to the embodiments. However, the embodiments of the invention can be modified in various ways. For example, the material for the polymer nanosheet 3 is not limited to those listed in the above embodiments. In fact, there may be employed various kinds of materials, provided that they are capable of forming a polymer nanosheet 3 allowing the electronic element 4 and others to be attached thereto through the intermolecular force. As for the material for the conductive wiring 5, there may be employed various kinds of materials as well, as long as they are conductive. Moreover, the method for forming the conductive wiring 5 is not limited to printing. In addition, although it is preferred that the power source 7 be disposed on the polymer nanosheet 3 or between the first polymer nanosheet 31 and the second polymer nanosheet 32, it may also be provided outside the electronic device 1 and connected to the conductive wiring 5 that is located inside the electronic device 1.

INDUSTRIAL APPLICABILITY

The electronic device 1 of the present invention is capable of measuring pulses and skin conductance, and even detecting perspiration, when attached to an object for attaching such as skin and an organ. Thus, the electronic device 1 of the invention can be used as a biomedical electronic device for elderly people and patients, and as a biomonitor electronic device for athletes. Further, an RFID tag may be installed as the electronic element 4. In such case, visitors with the electronic devices 1 attached to their skin, for example, can have themselves checked in at an entrance gate, since the electronic device 1 now functions as an alternative to a ticket. Moreover, the present invention can be applied to biological research in a way such that by attaching the electronic device 1 to an organ or a non-human animal or insect, their location information, for example, can be tracked. In addition, the present invention can also contribute to the traceability of a commercial product, by attaching to a product such as a food the electronic device 1 with information such as origins and producers already stored therein.

REFERENCE SIGNS LIST

1 Electronic device
3 Polymer nanosheet
4 Electronic element
5 Conductive wiring
6 Active part
7 Power source
8 Electrode
11 Substrate
12 Sacrifice layer
14 ink absorbing layer
21 Silver nanoparticles
31 First polymer nanosheet
32 Second polymer nanosheet

The invention claimed is:

1. A flexible electronic device comprising:
   an electronic element;
   a flexible polymer nanosheet having a self-supportability, and adhering to said electronic element and flexibly conforming to an outer surface of said electronic element in a manner such that one surface of said electronic element is entirely covered by said polymer nanosheet, said polymer nanosheet having a thickness of smaller than 1 μm and adhered to said electronic element through an intermolecular force and without an adhesive between said polymer nanosheet and said electronic element; and
   a conductive wiring formed on a surface of said polymer nanosheet, and electrically connected to an electrode of said electronic element through an intermolecular force between said conductive wiring and said electrode.

2. The flexible electronic device according to claim 1, wherein an ink absorbing layer is further provided on said polymer nanosheet, and said conductive wiring is printed on said ink absorbing layer.

3. The flexible electronic device according to claim 1, wherein said electronic element is an active part, and a power source for supplying power to said active part is further provided on said polymer nanosheet.

4. The flexible electronic device according to claim 1, wherein said polymer nanosheet is made of any one of polystyrene-isoprene-styrene, polydimethylsiloxane, silicone, polystyrene, polymethacrylate, polylactate, polylactic acid-glycolic acid copolymer, polyvinyl acetate, chitosan, alginic acid, cellulose acetate, hyaluronic acid, gelatin and collagen.

5. A flexible electronic device comprising:
   an electronic element;
   a first flexible polymer nanosheet and a second flexible polymer nanosheet each having a self-supportability, and each adhering to said electronic element, and each having a thickness of smaller than 1 μm, and each adhere to said electronic element through an intermolecular force and without an adhesive between said each polymer nanosheet and said electronic element and flexibly conform to an outer surface of said electronic element; and
   a conductive wiring formed on at least one of a surface of said first polymer nanosheet and a surface of said second polymer nanosheet, connected to an electrode of said electronic element through an intermolecular force between said conductive wiring and said electrode, and electrically connected to said electronic element,
   wherein said first polymer nanosheet and said second polymer nanosheet are in a close contact with and stick to each other without an adhesive through an intermolecular force between said first polymer nanosheet and said second polymer nanosheet, and said electronic element is sandwiched between said first polymer nanosheet and said second polymer nanosheet.

6. The flexible electronic device according to claim 5, wherein an ink absorbing layer is further provided on at least one of said first polymer nanosheet and said second polymer nanosheet, and said conductive wiring is printed on said ink absorbing layer.

7. The flexible electronic device according to claim 5, wherein said electronic element is an active part, and a power source for supplying power to said active part is further sandwiched between said first polymer nanosheet and said second polymer nanosheet.

8. The flexible electronic device according to claim 5, wherein each of said first polymer nanosheet and said second polymer nanosheet is made of any one of polystyrene-isoprene-styrene, polydimethylsiloxane, silicone, polystyrene, polymethacrylate, polylactate, polylactic acid-glycolic acid copolymer, polyvinyl acetate, chitosan, alginic acid, cellulose acetate, hyaluronic acid, gelatin and collagen.

9. The flexible electronic device according to claim 1, wherein said conductive wiring is made of at least one material selected from metal nanoparticles, semiconductor nanoparticles, a conductive polymer and a nano-carbon material.

10. The flexible electronic device according to claim 9, wherein said metal nanoparticles are composed of at least one of silver, gold, copper and nickel.

11. A method for manufacturing a flexible electronic device, comprising:
   a step of forming a first polymer nanosheet having a self-supportability on a substrate;
   a step of forming a conductive wiring on a surface of said first polymer nanosheet;
   a step of arranging an electronic element in a manner such that an electrode of said electronic element is capable of coming into contact with said conductive wiring;
   a step of bringing a second polymer nanosheet having a self-supportability into a close contact with said first polymer nanosheet to stick said second polymer nanosheet to said first polymer nanosheet through an intermolecular force with said electronic element and said conductive wiring being sandwiched therebetween, and thus electrically connecting said electronic element and said conductive wiring; and
   a step of separating said substrate from said first polymer nanosheet.

12. The method for manufacturing the flexible electronic device according to claim 11, wherein in the step of forming said first polymer nanosheet, after forming on said substrate a sacrifice layer capable of being dissolved by a solvent incapable of dissolving said first polymer nanosheet and said second polymer nanosheet, said first polymer nanosheet is then formed on said sacrifice layer; and in the step of separating said substrate, said sacrifice layer is dissolved by said solvent to separate said substrate from said first polymer nanosheet.

* * * * *